US00PP19310P2

(12) United States Plant Patent
Radler

(10) Patent No.: US PP19,310 P2
(45) Date of Patent: Oct. 7, 2008

(54) CLIMBING ROSE PLANT NAMED 'RADWIN'

(50) Latin Name: *Rosa hybrida*
Varietal Denomination: Radwin

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/889,031

(22) Filed: Aug. 8, 2007

(51) Int. Cl.
*A01H 5/00* (2006.01)

(52) U.S. Cl. ..... Plt./115
(58) Field of Classification Search ..... Plt./115
See application file for complete search history.

*Primary Examiner*—Kent L Bell
(74) *Attorney, Agent, or Firm*—Buchanan Ingersoll & Rooney PC

(57) ABSTRACT

A new and distinct variety of rose plant is provided which forms in abundance on a substantially continuous basis attractive single blossoms that are red in coloration. The vegetative is vigorous and the growth habit is upright and climbing. Attractive ornamental green foliage having a satiny finish is formed in abundance. Excellent resistance with respect to blackspot is displayed. The new variety is particularly well suited for growing as distinctive ornamentation in parks, gardens, and residential settings.

5 Drawing Sheets

Botanical/commercial classification: *Rosa hybrida*/ Climbing Rose Plant.
Varietal denomination: cv. Radwin.

SUMMARY OF THE INVENTION

The new variety of *Rosa hybrida* climbing rose plant of the present invention was created at Greenfield, Wis., U.S.A., by artificial pollination during 1997 wherein two parents were crossed which previously had been studied in the hope that they would contribute the desired characteristics. The female parent (i.e., the seed parent) was the 'Radliv' variety (non-patented in the United States). The male parent (i.e., the pollen parent) of the new variety was the 'Radkoswe' variety (non-patented in the United States). The parentage of the new variety can be summarized as follows:

'Radliv'×'Radkoswe'.

The seeds resulting from the above pollination were sown during 1998 and small plants were obtained which were physically and biologically different from each other. Selective study resulted in the identification of a single plant of the new variety.

It was found that the new climbing rose plant of the present invention possesses the following combination of characteristics:

(a) abundantly and substantially continuously forms attractive single blossoms that are red in coloration, (b) exhibits an upright and climbing growth habit, (c) forms vigorous vegetation, (d) abundantly forms attractive ornamental green foliage with a satiny finish, (e) exhibits excellent resistance to blackspot, and (f) exhibits excellent cold hardiness.

A new climbing rose variety is provided having attractive red blossoms combined with a repeat blooming character and resistance to blackspot.

The new variety well meets the needs of the horticultural industry. It can be grown to advantage as attractive ornamentation in parks, gardens, public areas, and in residential settings. The new variety is particularly well suited for providing attractive ornamentation as a climbing rose plant when grown on a support. The red blossoms contrast nicely with the satiny green foliage.

The new variety of the present invention can be readily distinguished from its ancestors. More specifically, the 'Radliv' variety is a dissimilar shrub rose plant that is less vigorous and less floriferous. Also, the winter hardiness of the new variety is superior to that of the 'Radliv' variety, and the foliage is more densely borne. The 'Radkoswe' variety tends to be only once blooming during the season, is less resistant to diseases, and has a lesser ability to retain flower coloration late in the growing season during the fall.

The characteristics of the new variety have been found near West Grove, Pa., U.S.A., and elsewhere, to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radwin'.

BRIEF DESCRIPTION OF THE PHOTOGRAPHS

The accompanying photographs show, as nearly true as it is reasonably possible to make the same in color illustrations of this character, typical specimens of the new variety.

FIG. 1 shows a close view of a typical blossom of the new variety. The plant which produced the blossom had been budded on Dr. Huey rootstock, was approximately three years of age, and was growing in a three-gallon container at West Grove, Pa., U.S.A.

DETAILED DESCRIPTION

Figure 1:
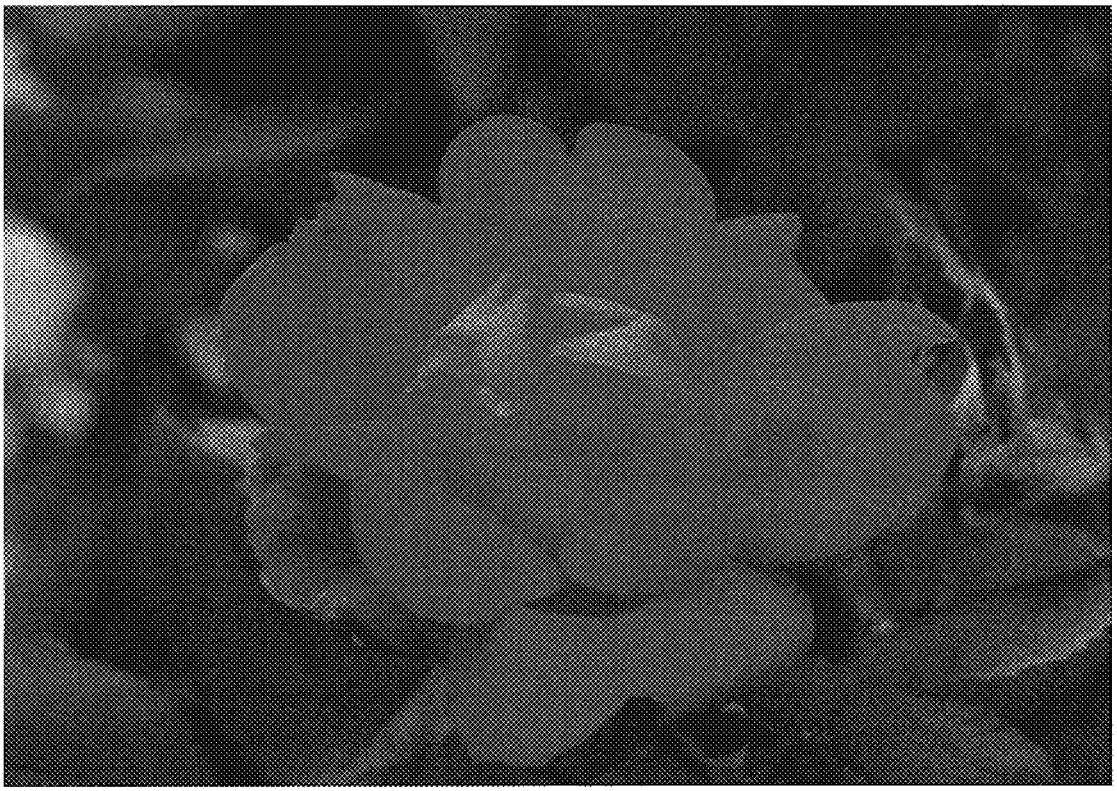
Figure 2:
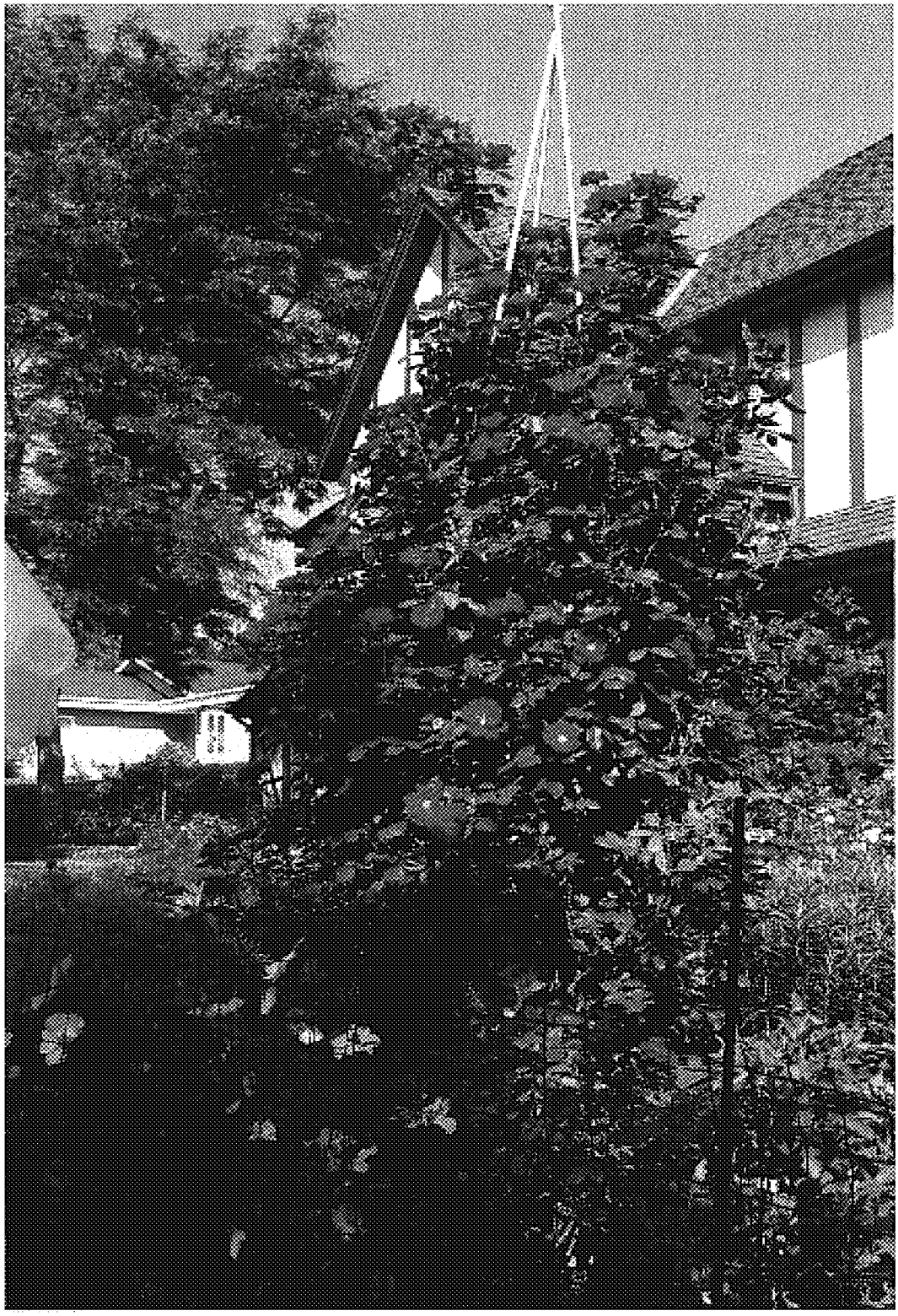
FIG. 2 shows the original plant of the new variety during June while growing on a support. The plant was approximately seven years of age, and was growing at Greenfield, Wis., U.S.A.

The chart used in the identification of colors is that of The Royal Horticultural Society (R.H.S. Colour Chart), London, England. The description is based on the observation of three-year-old specimens of the new variety during June while growing outdoors in containers near West Grove, Pa., U.S.A.

Class: Climbing Rose.

Plant:

*Height.*—Approximately 4 to 5 feet on average at the end of the growing season, and commonly assumes a mature height of approximately 8 feet.

*Width.*—Approximately 3 to 4 feet on average at the end of one growing season, and commonly continues to display approximately the same width at full maturity.

*Habit.*—Upright and climbing.

Branches:

*Color.*—New shoots: commonly between Green Group 139C and Yellow-Green Group 144A and often heavily flushed with Greyed-Purple Group 183B and Greyed-Purple Group 187B when exposed to the sun. Major stems: commonly near Yellow-Green Group 144A. Branches: commonly between Green Group 139B and Yellow-Green Group 144A, and sometimes lightly blushed with Greyed-Purple Group 183B and Greyed-Purple Group 187B when exposed to the sun.

*Caliper.*—Canes are of heavy caliper for the class.

*Thorns.*—On new shoots: commonly bear several large prickles which are approximately 0.9 to 1.4 cm in length that are moderately angled downward with a narrow moderately long base measuring approximately 1 cm in length and approximately 4 mm in width having a coloration between Greyed-Purple Group 183A and Greyed-Purple Group 187A. A few small prickles of a similar shape and coloration also may be present. On major stems: commonly bear several large prickles which are approximately 0.9 to 1.4 cm in length are moderately angled downward with a narrow moderately long base measuring approximately 1 cm in length and approximately 4 mm in width having a coloration between Greyed-Orange Group 164A and Greyed-Orange Group 165A. A few small prickles of a similar shape and coloration also may be present. Branches: commonly bear several large prickles which are approximately 0.9 to 1.4 cm in length that are moderately angled downwards with a narrow moderately long base measuring approximately 1 cm in length and approximately 4 mm in width having a coloration between Greyed-Yellow Group 161A and Greyed-Orange Group 164B, and often lightly suffused with between Greyed-Red Group 181A and Greyed-Purple Group 184B. A few small prickles of similar shape and coloration also may be present.

Leaves:

*Leaflet number.*—3, 5, and 7, borne very abundantly.

*Leaflet texture.*—Moderately firm, moderately rugose, and with a satiny finish.

*Leaflet size.*—Commonly approximately 5 to 6 cm in length on average, and approximately 3 to 4 cm in width on average.

*Leaflet shape.*—Moderately oval to somewhat ovate with acute to somewhat acuminate apices, and rounded bases.

*Leaflet margins.*—Commonly serrate.

*Leaf size.*—Commonly approximately 9.5 to 14.5 cm in length, and approximately 10 to 12 cm in width at the widest point.

Figure 3:
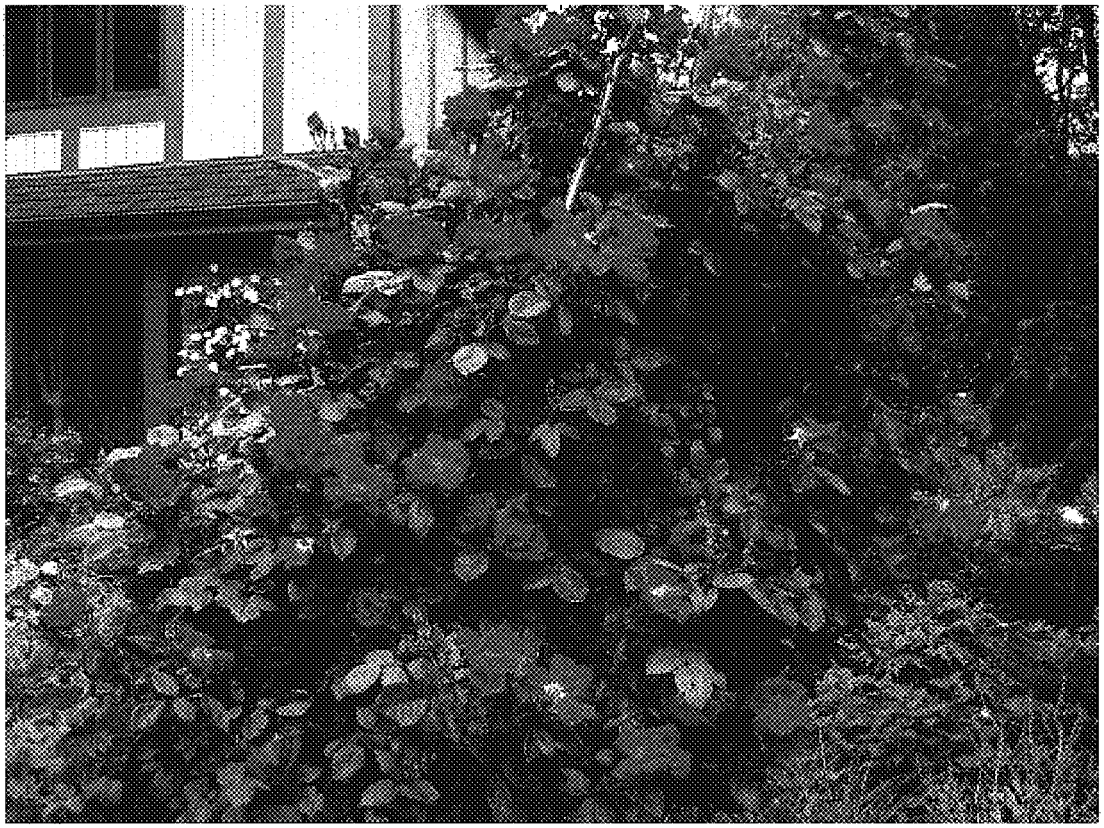
FIG. 3 shows a closer view of the original plant of the new variety during June. The abundant dense foliage is apparent.
Figure 4:
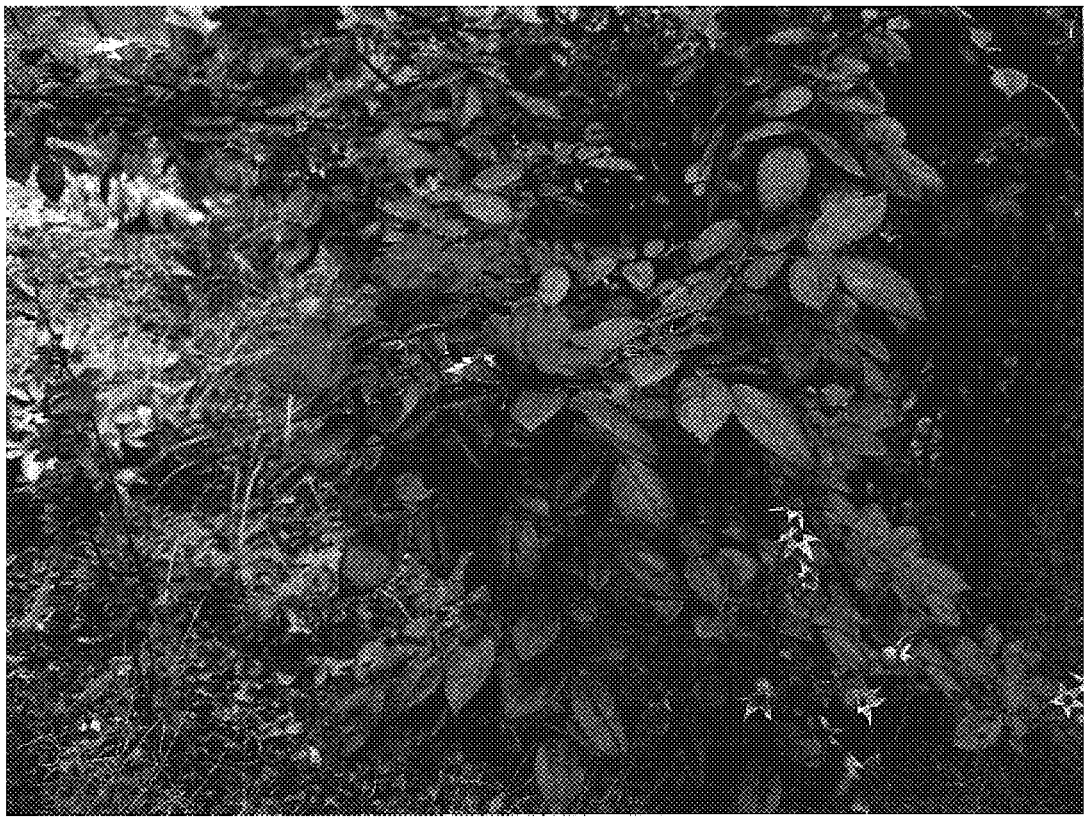
FIG. 4 shows purplish foliage coloration of the original plant of the variety while continuing to flower during October. Some hips are shown at the lower right.

*Color.*—Young leaves: upper surfaces commonly are between Green Group 139B and Yellow-Green Group 147A and are often moderately suffused with between Greyed-Purple Group 183B and Greyed-Purple Group 187C, and under surfaces commonly are between Green Group 139C and Yellow-Green Group 147B. Mature leaves: upper surfaces commonly are between Green Group 139B and Yellow-Green Group 147C, and under surfaces commonly are between Yellow-Green Group 147B and 147C. Fall leaves: during the fall, particularly when grown in cooler environments, the leaves may assume a purplish coloration similar to that shown in FIG. 3.

*Stipules.*—Configuration: with moderately narrow medium to long points that commonly turn out at an angle more than 45 degrees. Length: commonly approximately 1.8 cm. Width: commonly approximately 0.8 cm at the widest portion of the body.

*Rachis.*—Moderately smooth, average in caliper, the upper surface commonly is moderately grooved with some stipitate glands and tiny hairs on the edges of the grooves, and the underside commonly is rough with a few stipitate glands and numerous small prickles.

Inflorescence:

*Peduncle.*—Length: commonly approximately 3.5 cm in length, and typically erect. Diameter: commonly approximately 2 mm. Texture: moderately smooth with some stipitate glands and a few hairs. Color: commonly between Yellow-Green Group 144B and 144C, and sometimes moderately suffused with between Greyed-Purple Group 183B and 183C. Texture: the inner surface is lined and edged with very fine wooly tomentum, and the margins commonly are lined with a few stipitate glands and hairs. Color: on the outer surface commonly is near Yellow-Green Group 144B towards the base and suffused with Greyed-Purple Group 183C towards the tip, and on the inner surface commonly is near Yellow-Green Group 145D. Number: five.

*Buds.*—Shape: commonly very pointed and urn-shaped. Length: before the calyx breaks commonly approximately 1 to 1.5 cm. Diameter: before the calyx breaks commonly approximately 1 cm at the widest point. Texture: commonly bears numerous stipitate glands and some hairs. Color (before the calyx breaks): commonly between Yellow-Green Group 144A and 144B and often moderately suffused with Greyed-Purple Group 183B and 183C.

*Flower.*—Form: Single. Shape: informal, when partially open very high centered with loosely spiraled petals and petal edges that are very slightly reflexed outward, and when fully open somewhat flattened with petals that are moderately flattened to undulated with slightly reflexed outward petal edges. Diameter: commonly approximately 7 to 7.5 cm on average when fully open. Petal texture: medium thickness with moderately velvety to slightly satiny on the upper surface, and mostly satiny to somewhat satiny on the under surface. Color (newly opened flower): Upper surface: Red Group 46A with a small zone of Yellow Group 3A at the base. Under surface: Red Group 46B commonly with a small zone of Yellow Group 3A at the base. Color (three-day-old): Upper surface: primarily Red Group 46C commonly with a small zone of Yellow Group 3C at the base. Under surface: Red Group 46D with a small zone of Yellow Group 3C at the base. Lastingness: commonly approximately 4 or 5 days or more on the plant, and approximately the same time when cut and placed in a vase. Fragrance: mild rose. Petal form: substantially round to very broadly obovate. Petal number: commonly approximately 8 to 10 on average. Petal base: commonly rounded. Petal apex: commonly rounded and sometimes notched with one or two notches. Petal size: commonly approximately 30 to 35 mm in length, and approximately 40 to 45 mm in width. Petal margin: mostly entire, and occasionally becoming slightly undulate towards the apex. Petaloid number: commonly approximately 1 to 2 per flower on average. Petaloid length: commonly approximately 30 mm. Petaloid width: commonly approximately 16 mm at the widest point. Petal drop: very good, the petals commonly drop cleanly and freely. Stamen number: approximately 155 to 160 on average arranged regularly about the pistils. Anthers: medium-sized and commonly measure approximately 2 mm×1 mm, and commonly open at approximately the same time. Anther color: commonly between Yellow Group 13C and Yellow-Orange Group 16A when immature, and between Greyed-Orange Group 163A and Greyed-Orange Group 165A when mature. Filament length: medium to long, and commonly approximately 7 to 9 mm, and most bear anthers. Filament color: Yellow Group 13C and sometimes moderately suffused with Red Group 43C. Pollen: commonly is present in a moderate to abundant quantity and commonly is near Yellow Group 13B in coloration. Pistils: commonly approximately 63 on average. Stigma color: commonly between Yellow Group 8D and Yellow Group 9D. Styles: moderately uneven, relatively short, commonly approximately 4.5 mm in length, approximately 0.25 mm in caliper, and moderately bunched. Style color: commonly near Yellow Group 8D suffused with Red Group 46D. Ovaries: typically enclosed in the calyx.

*Hips.*—Moderately ovoid to globular in shape, moderately smooth with thick fleshy walls, average in length, the sepals commonly persist, and typically are between Orange Group 28A and Orange-Red Group 33A in coloration when ripe.

*Seeds.*—Medium in size, and commonly number approximately 7 to 11 per hip.

Development:

*Vegetation.*—Vigorous and strong.

*Blossoming.*—Very abundant and substantially continuous during the growing season.

*Resistance to diseases.*—Excellent with respect to blackspot, and powdery mildew when compared to commercial rose varieties being grown near West Grove, Pa., U.S.A., and Milwaukee, Wis., U.S.A., during the past three years.

*Cold hardiness.*—Excellent, and has proven to grown well down to U.S.D.A. Hardiness Zone No. 5.

Figure 5:
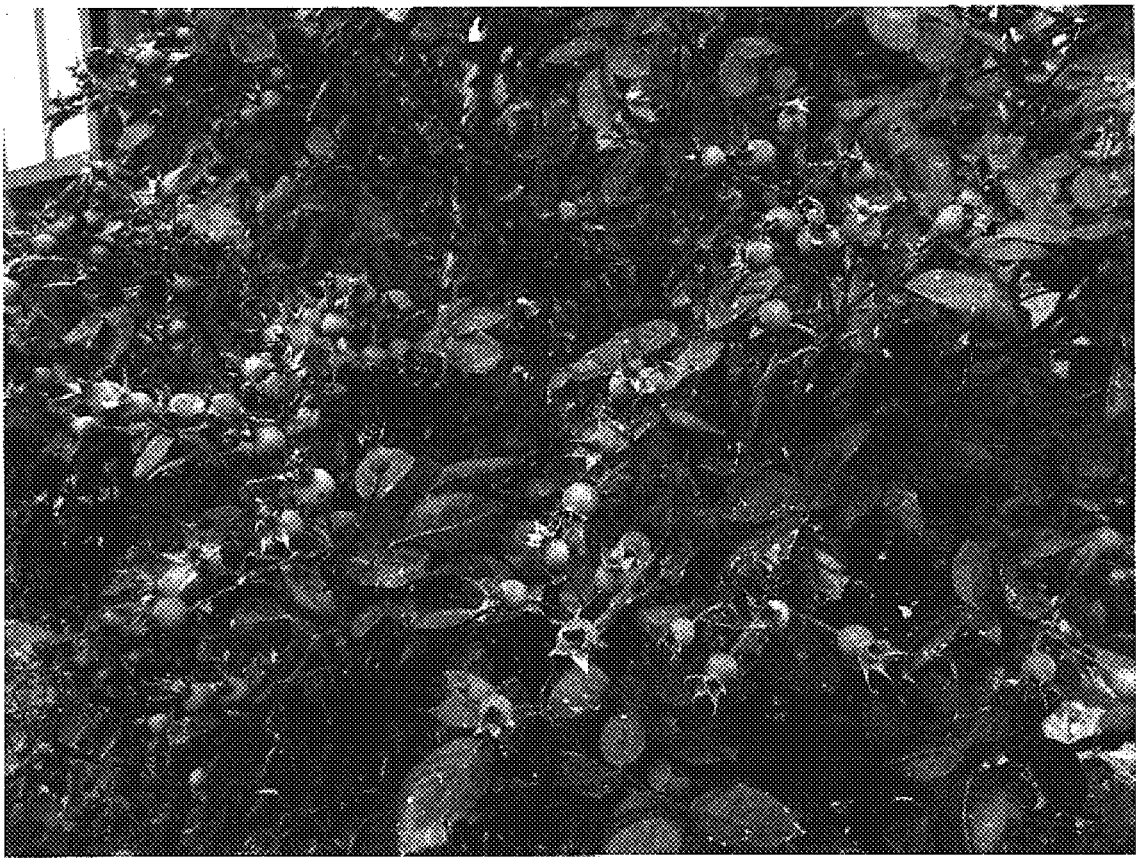
FIG. 5 shows a closer view of typical hips of the new variety during November when formed on the original plant of the new variety.

*Formation of hips/seeds.*—Hips and seeds are formed. The hips are large, substantially round and yellow-orange in coloration as shown in FIG. 5.

The new 'Radwin' variety has not been observed under all possible environmental conditions to date. Accordingly, it is possible that the phenotypic expression may vary somewhat with changes in light intensity and duration, cultural practices, and other environmental conditions.

I claim:

1. A new and distinct climbing rose plant characterized by the following combination of characteristics:

(a) abundantly and substantially continuously forms attractive single blossoms that are red in coloration, (b) exhibits an upright and climbing growth habit, (c) forms vigorous vegetation, (d) abundantly forms attractive ornamental green foliage with a satiny finish, (e) exhibits excellent resistance to blackspot, and (f) exhibits excellent cold hardiness;

substantially as herein shown and described.

* * * * *